United States Patent [19]

Chabala et al.

[11] Patent Number: 5,120,729

[45] Date of Patent: * Jun. 9, 1992

[54] BETA-LACTAMS AS ANTIHYPERCHOLESTEROLEMICS

[75] Inventors: John C. Chabala, Westfield, N.J.; Michael N. Chang, Newtown, Pa.; Yuan-Ching P. Chiang, Piscataway, N.J.; James V. Heck, Scotch Plains, N.J.; Kathryn L. Thompson, Westfield, N.J.; Shu S. Yang, Bridgewater, N.J.

[73] Assignee: Merck & Co., Inc., Rahway, N.J.

[*] Notice: The portion of the term of this patent subsequent to Jan. 8, 2008 has been disclaimed.

[21] Appl. No.: 540,992

[22] Filed: Jun. 20, 1990

[51] Int. Cl.$^5$ .................. A61K 31/395; C07D 401/12; C07D 205/08; C07D 403/120
[52] U.S. Cl. ..................... 514/210; 540/355
[58] Field of Search .................. 540/355; 514/210

[56] References Cited

U.S. PATENT DOCUMENTS

| | | | |
|---|---|---|---|
| 4,675,399 | 6/1987 | Miller | 540/355 |
| 4,680,391 | 7/1987 | Firestone et al. | 540/335 |
| 4,778,883 | 10/1988 | Yoshioka et al. | 540/200 |
| 4,806,564 | 2/1989 | Chabala et al. | 514/449 |
| 4,816,477 | 3/1989 | Girotra et al. | 514/449 |
| 4,847,271 | 7/1989 | Chabala et al. | 514/336 |
| 4,983,597 | 1/1991 | Yang et al. | 540/355 |

OTHER PUBLICATIONS

CA: 105052r, vol. 99, 1983.

Primary Examiner—Mukund J. Shah
Assistant Examiner—Jyothsna Venkat
Attorney, Agent, or Firm—Joseph F. DiPrima; Melvin Winokur

[57] ABSTRACT

This application relates to compounds of formula (I), which are useful as antihypercholesterolemic agents.

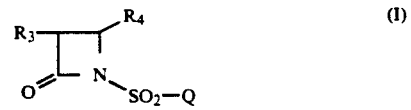

19 Claims, No Drawings

BETA-LACTAMS AS ANTIHYPERCHOLESTEROLEMICS

BACKGROUND OF THE INVENTION

Hypercholesterolemia is known to be one of the prime risk factors for ischemic cardiovascular disease, such as arteriosclerosis. Bile acid sequestrants have been used to treat this condition; they seem to be moderately effective but they must be consumed in large quantities, i.e., several grams at a time, and they are not very palatable.

MEVACOR ® (lovastatin), now commercially available is one of a group of very active antihypercholesterolemic agents that function by limiting cholesterol biosynthesis by inhibiting the enzyme, HMG-CoA reductase. Another approach to limiting cholesterol biosynthesis is through inhibition of the enzyme HMG-CoA synthase.

U.S. Pat. No. 4,806,564 discloses certain $\beta$-lactones of formula (i)

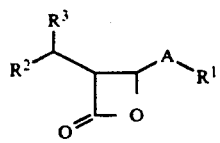

which are useful as antihypercholesterolemic agents and are believed to function by inhibiting HMG-CoA synthase. Additional $\beta$-lactones which have antihypercholesterolemic activity are disclosed in U.S. Pat. Nos. 4,816,477 and 4,847,271.

DETAILED DESCRIPTION OF THE INVENTION

The present invention is directed to compounds of structural formula (I):

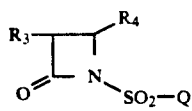

wherein:
Q is
 a) $C_{1-5}$ alkyl;
 b) $C_{6-10}$ aryl or $C_{4-10}$ heteroaryl including one heteroatom selected from N, O, or S;
 c) $C_{7-15}$ aralkyl or $C_{7-15}$ heteroaralkyl;
 d) $C_{6-10}$ aryl or $C_{6-10}$ heteroaryl substituted with W;
 e) $C_{7-15}$ aralkyl or $C_{7-15}$ heteroaralkyl wherein the aryl or heteroaryl moiety is substituted with W;
 f) OH;
$R_3$ is
 a) H;
 b) $C_{1-5}$ alkyl;
 e) $C_{1-5}$ alkoxyCH$_2$—;
$R_4$ is —(CH$_2$)$_n$ R;
R is a) 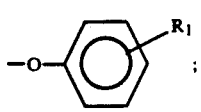

b) 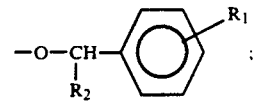

c) 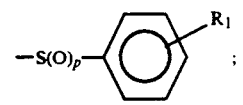

d) —O—$C_{1-5}$ alkyl;
e) halogen; or

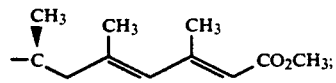

$R_1$ is
 a) H;
 b) $C_{1-5}$ alkyl;
 c) —CO$_2$C$_{1-5}$ alkyl;
$R_2$ is
 a) H;

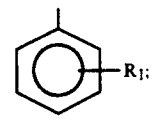

n is 1 to 4;
p is 0 to 2;
halogen is F, Cl, Br or I;
W is
 a) $C_{1-5}$ alkyl;
 b) $C_{1-5}$ alkoxy;
 c) —CO$_2$C$_{1-5}$ alkyl;
 d) —NO$_2$.

One embodiment of the present invention is the compounds of formula (I) wherein n is 1.

In one class of this embodiment are those compounds wherein:
$R_3$ is H; and
R is a) 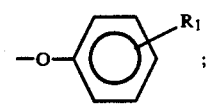

b) 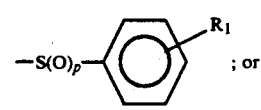; or c) halogen; and
Q is

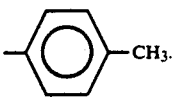

Exemplifying this class are the compounds of formula (I) described in Table I.

TABLE I

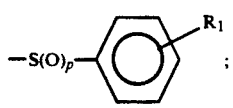

| R | Configuration at 4-Position | $IC_{50}$ |
|---|---|---|
| i) −S−⟨phenyl⟩ | S | $7.0 \times 10^{-8}$ |
| ii) −S(O)−⟨phenyl⟩ | S | $1.2 \times 10^{-7}$ |
| iii) −SO$_2$−⟨phenyl⟩ | S | $1.2 \times 10^{-7}$ |
| iv) −O−⟨phenyl⟩−CO$_2$CH$_3$ | S | $4.6 \times 10^{-8}$ |
| v) I | S | $8.2 \times 10^{-7}$ |

In a second class of this embodiment are those compounds of formula (I) wherein $R_3$ is $C_{1-5}$ alkyl and R is a) −S(O)$_p$−⟨phenyl⟩−$R_1$ ;

b) $C_{1-5}$ alkoxy;

c) halogen; and

Q is

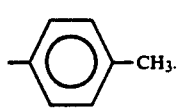

Exemplifying this class are the compounds of formula (I) described in Table II.

TABLE II

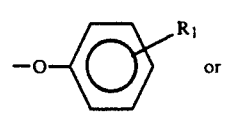

| | R | Configuration at the 3,4 position | $IC_{50}$ |
|---|---|---|---|
| i) $R_3$ = CH$_3$CH$_2$− | −S−⟨phenyl⟩ | cis | $1.2 \times 10^{-7}$ |
| ii) CH$_3$CH$_2$− | −O−CH$_3$ | cis | $6.7 \times 10^{-8}$ |
| iii) CH$_3$CH$_2$− | F | cis | $6.0 \times 10^{-8}$ |

In a second embodiment of the present invention are those compounds of formula (I) wherein n is 2.

In one class of this embodiment are those compounds wherein:

$R_3$ is H;

R is a) −O−⟨phenyl⟩−$R_1$ or b) −O−CH($R_2$)−⟨phenyl⟩−$R_1$ ; and

Q is

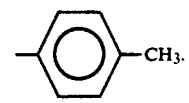

Exemplifying this class are the compounds in Table III.

TABLE III

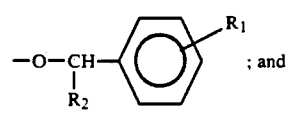

| R | $IC_{50}$ |
|---|---|
| i) −O−⟨phenyl⟩−CO$_2$CH$_3$ | $6.6 \times 10^{-8}$ |
| ii) −O−CH$_2$−⟨phenyl⟩ | $9.0 \times 10^{-8}$ |

TABLE III-continued

[Structure: β-lactam with CH₂CH₂R substituent, N-SO₂-p-tolyl]

| R | IC$_{50}$ |
|---|---|
| iii) $-O-CH(C_6H_5)_2$ (benzhydryloxy) | $6.1 \times 10^{-8}$ |

In the second class of this embodiment are those compounds wherein:
  $R_3$ is $CH_3CH_2-$ or $CH_3OCH_2-$; and
  R is a) 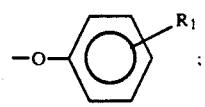

b) 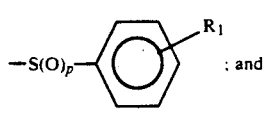 ; and

Q is

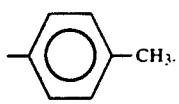

Exemplifying this class are the compounds of Table IV.

TABLE IV

[Structure: β-lactam with R₃ and CH₂CH₂R substituents, N-SO₂-p-tolyl]

| | R₃ | R | Configuration at the 3,4 position | IC$_{50}$ |
|---|---|---|---|---|
| i) | $CH_3CH_2-$ | $-O-C_6H_4-CO_2CH_3$ | cis | $6.5 \times 10^{-8}$ |
| ii) | $CH_3OCH_2-$ | $-O-C_6H_4-CO_2CH_3$ | trans | $1.4 \times 10^{-6}$ |
| iii) | $CH_3CH_2-$ | $-SO_2-C_6H_5$ | cis | $6.4 \times 10^{-7}$ |

A third embodiment of the present invention is the compounds of formula (I) wherein n is 3.

In one class of this embodiment are those compounds wherein:
  $R_3$ is H; and
  R is a) 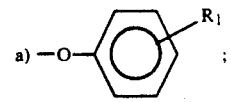 ;

b) halogen; and

Q is

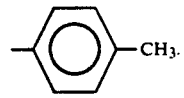

Exemplifying this class are the compounds of Table V.

TABLE V

[Structure: β-lactam with CH₂CH₂CH₂R substituent, N-SO₂-p-tolyl]

| R | IC$_{50}$ |
|---|---|
| i) $-O-C_6H_4-CO_2CH_3$ | $1.9 \times 10^{-7}$ |
| ii) $-O-C_6H_5$ | $1.4 \times 10^{-7}$ |

TABLE V-continued

[Structure: β-lactam with CH2CH2CH2R substituent, N-SO2-C6H4-CH3]

| R | IC50 |
|---|---|
| iii) Br | $1.3 \times 10^{-7}$ |

A fourth embodiment of the present invention is the compounds of formula (I) wherein n is 4.
In one class of this embodiment
$R_3$ is H or $C_{1-5}$ alkoxyCH$_2$— and
R is

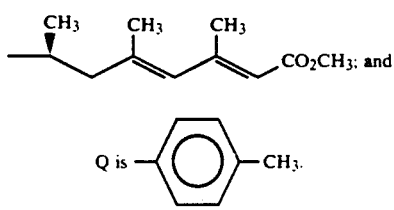

Q is [para-tolyl group]

Exemplifying this class is the compound of Table VI.

TABLE VI

[Structure as shown with R3, β-lactam ring, polyene chain terminating in CO2Me, N-SO2-tolyl]

| | IC50 |
|---|---|
| i) $R_3$ is $CH_3OCH_2$— | $3.6 \times 10^{-6}$ |

The alkyl groups referred to throughout this specification may be straight chain or branched. Halogen or halo means fluoro, chloro, bromo or iodo.

The compounds of the present invention may be prepared according to the methodology in Schemes I-V. Compounds wherein n is 1 and $R_3$ is hydrogen are prepared following Scheme I; for those compounds wherein n is 1 and $R_3$ is alkyl Scheme II is employed. Scheme III provides a sequence for those compounds wherein n is 2 or 3 and $R_3$ is hydrogen. Scheme IV provides direction to those compounds wherein n is 2 and $R_3$ is alkyl. Scheme V provides enablement for those compounds where n is 4.

SCHEME I

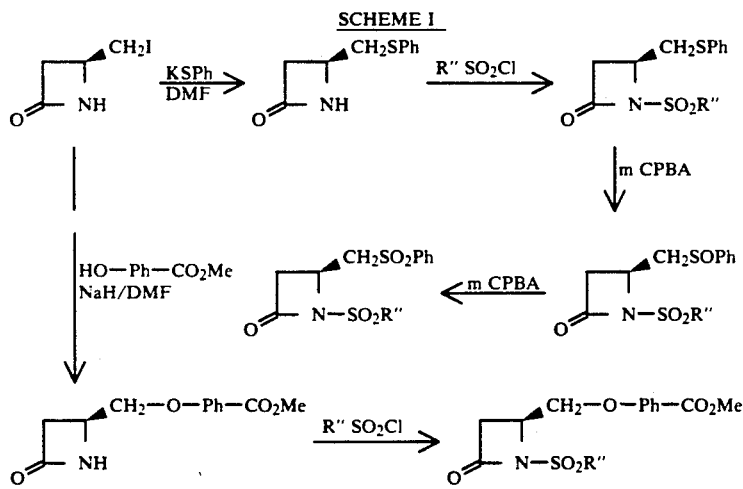

SCHEME II

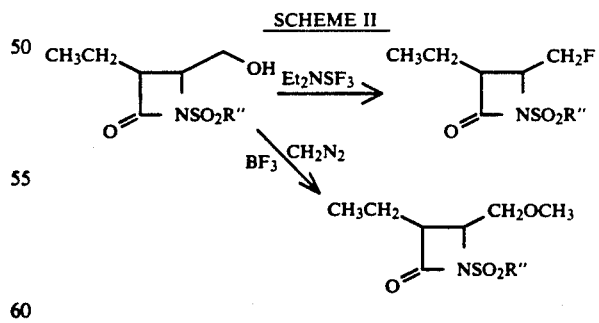

SCHEME III

[Reactions:
allyl-CH2CH2Br + HO—Ph—CO2Me —K2CO3→ allyl-CH2CH2—O—Ph—CO2Me
allyl-CH2CH2-OH + BrCH2—Ph —NaH→ allyl-CH2CH2—O—CH2—Ph]

-continued
SCHEME III
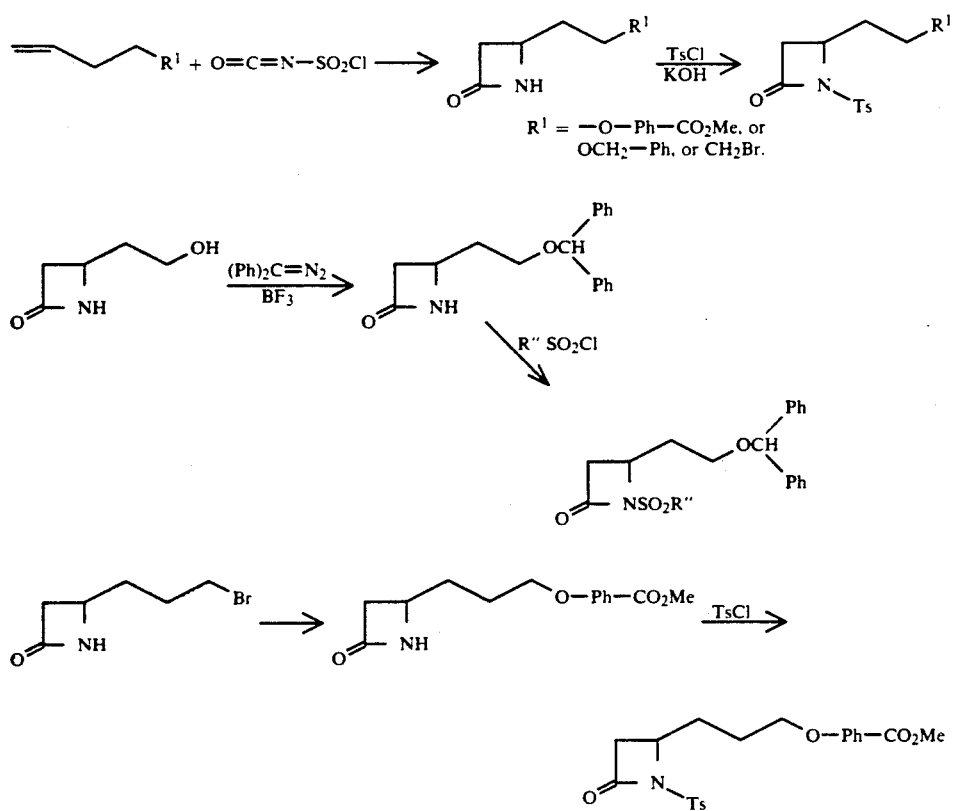
SCHEME IV
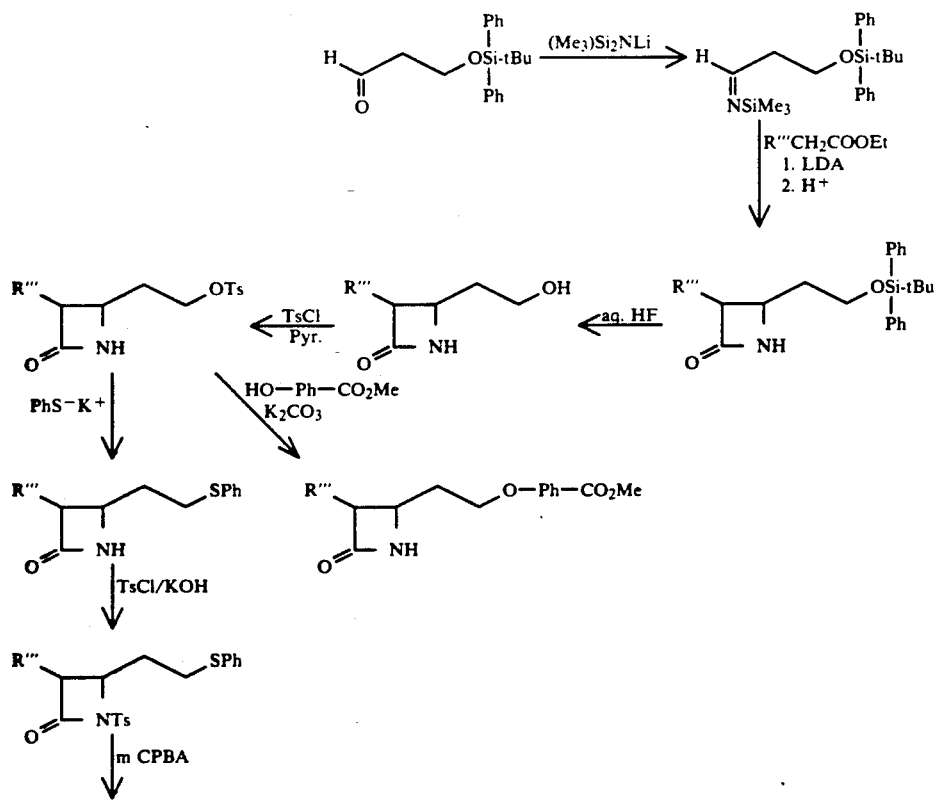

SCHEME IV
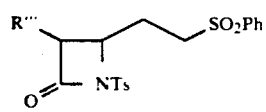
SCHEME V
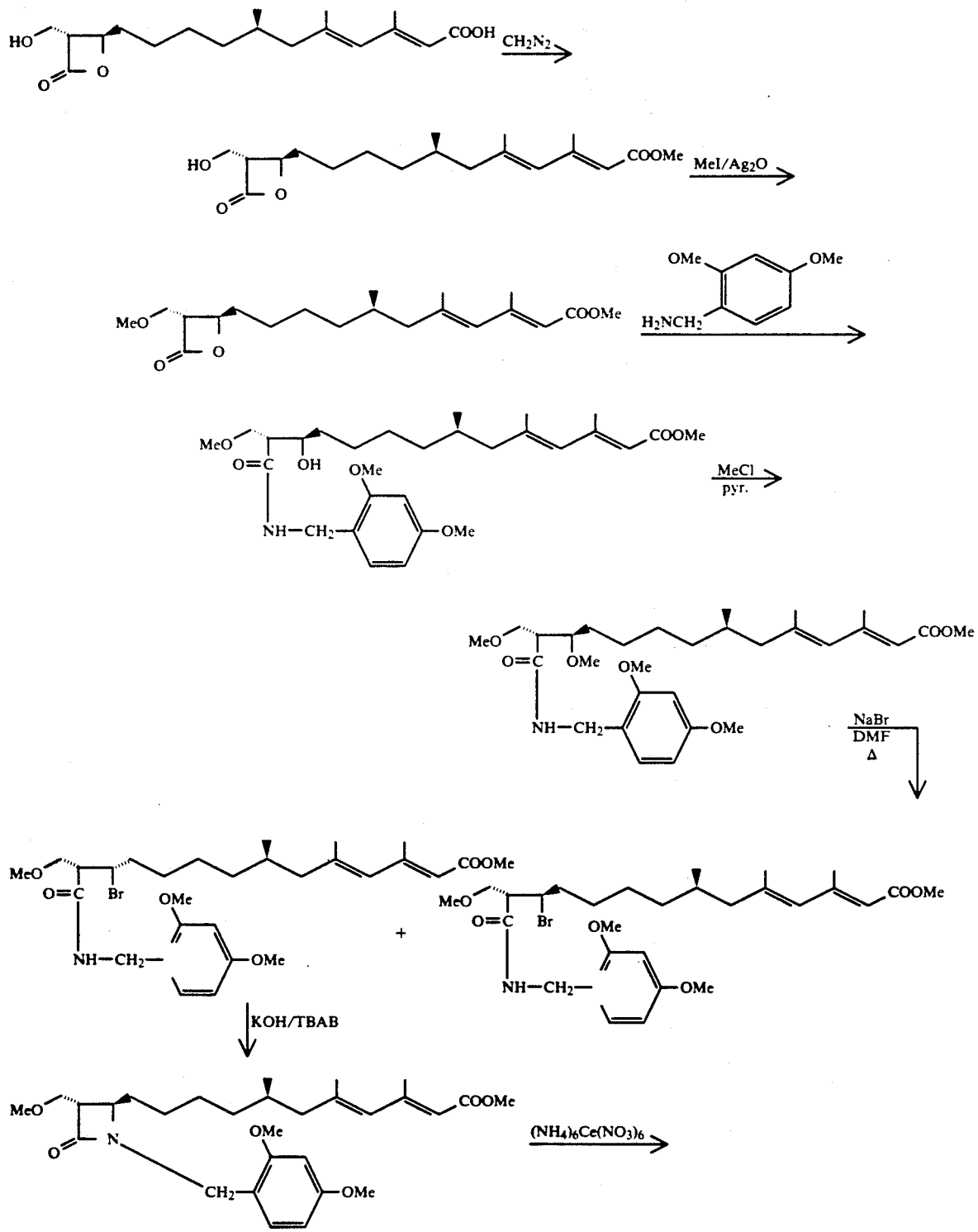

-continued
SCHEME V

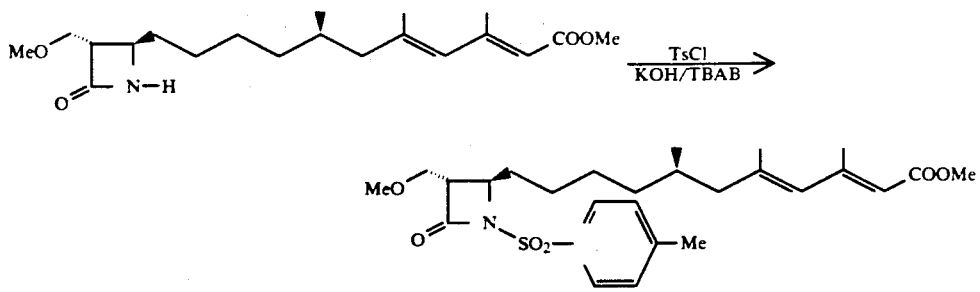

The present invention is also directed to a method of inhibiting cholesterol biosynthesis which comprises the administration to a subject in need of such treatment a nontoxic, therapeutically effective amount of a compound represented by the following general structural formula (I) and pharmaceutically acceptable salts thereof.

The present invention is also directed to a method of inhibiting the activity of HMG-CoA synthase enzyme which comprises the administration to a subject in need of such treatment a nontoxic, therapeutically effective amount of a compound represented by the general structural formula (I) and pharmaceutically acceptable salts thereof.

Specifically the compounds of this invention are useful as antihypercholesterolemic agents for the treatment of arteriosclerosis, hyperlipidemia, familiar hypercholesterolemia and the like diseases in humans. They may be administered parenterally in the form of a capsule, a tablet, an injectable preparation or the like. Doses may be varied, depending on the age, severity, body weight and other conditions of human patients but daily dosage for adults is within a range of from about 20 mg to 2000 mg (preferably 20 to 100 mg) which may be given in two to four divided doses. Higher doses may be favorably employed as required.

The pharmaceutically acceptable salts of the compounds of this invention include those formed from cations such as sodium, potassium, aluminum, calcium, lithium, magnesium, zinc, and from bases such as ammonia, ethylenediamine, N-methylglucamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)aminomethane, and tetramethylammonium hydroxide.

The compounds of this invention may also be coadministered with pharmaceutically acceptable nontoxic cationic polymers capable of binding bile acids in a non-reabsorbable form in the gastrointestinal tract. Examples of such polymers include cholestyramine, colestipol and poly[methyl-(3-trimethylaminopropyl)iminotrimethylene dihalide]. The relative amounts of the compounds of this invention and these polymers is between 1:100 and 1:15,000.

The intrinsic HMG-CoA synthase inhibition activity of the compounds of this invention is measured by the standard in vitro protocol described below:

The livers from male Charles River CD rats (225-350 g) were homogenized in 0.25M sucrose which was adjusted with phenylmethylsulfonylfluoride (PMSF) and N-p-tosyl-l-lysine chloromethyl ketone (TLCK) so that the final concentration of each was 50 and 25 mg/ml, respectively. The homogenate was centrifuged at 15,000×g for 20 minutes, the supernatant filtered through a fine nylon screen to remove most of the fat layer and recentrifuged at 100,000×g for 1 hour. This supernatant was removed and 1M potassium phosphate, dithiothreitol (DTT) and ethylene glycolbis(β-aminoethyl ether)-N,N,N',N'-tetraacetic acid (EGTA) added to give a final concentration of 0.1M (pH 7.2), 0.5 mM and 0.1 mM, respectively. Solid ammonium sulfate was added to 50% saturation to the protein solution, it was centrifuged at 15,000×g and the supernatant discarded. This precipitated protein could be stored at −70° C. for at least one month with very little loss of activity. The ammonium sulfate precipitate was dissolved in an minimal amount of 0.06M potassium phosphate buffer (pH 7.2) containing 0.5 mM dithiothreitol and 0.1 mM EGTA (referred to as 0.06M phosphate buffer) and dialyzed overnight against 2 liters of the same buffer to remove the ammonium sulfate and to inactivate HMG-CoA lyase [Clinkenbeard, et al., J. Biol. Chem. 250, 3108-3116(1975)].

The dialyzed extract was added to a column of DEAE-52 (Whatman) which had been equilibrated with 0.06M phosphate buffer (10 mg of protein to 1 ml bed volume of the resin). The DEAE-cellulose was eluted with 0.06M phosphate buffer until the optical density at 280 nm was essentially zero. This fraction contained the β-ketoacetyl-CoA thiolase activity. The HMG-CoA synthase was eluted from the column with 0.1M phosphate buffer (pH 7.2) containing 0.5 mM DTT and 0.1 mM EGTA, and was virtually free of all thiolase activity. The protein was precipitated by the addition of ammonium sulfate to give 50% saturation. This solution was stirred for 10 minutes at 4° C. and the precipitate collected by centrifugation at 15,000 rpm for 10 minutes. The supernatant was discarded and the precipitate dissolved in a minimum of 0.06M phosphate buffer, pH 7.2 (about 10 ml) and the enzyme stored at −80° C.

HMG-CoA Synthase Inhibition Assay

Enzyme protein (ca. 24 mg) was added to a solution containing 117 μM Tris-HCl (pH 8.0), 11.7 μM MgCl$_2$, 1.17 μM ethylenediaminetetraacetic acid (EDTA), 0.58 μM dithiothreitol, and the indicated concentrations of the test compound (added as a 2 mg/ml solution in dimethylsulfoxide). The incubation took place in a volume of 0.085 ml at 30° in a shaking water bath. After 5 minutes, 15 ml of a solution containing acetoacetyl-CoA and 0.1 μCi of 1-[$^{14}$C]-acetyl-CoA was added to give a final concentrations of 0.1 and 0.4 μM, respectively. The incubation was continued for 10 more minutes and the reaction stopped by the addition of 50 ml of the assay mixture to 0.2 ml of 6N HCl in a glass scintillation vial. The vial was heated for 1 hour at 120° after which time 0.2 ml more of 6N HCl was again added to each vial and the heating continued for another hour. Following this, 1.0 ml of 0.9% saline was added to each vial and finally 10 ml of scintillation liquid. Radioactivity was determined in a Packard Tri-Carb liquid scintillation counter.

Percent inhibition is calculated by the formula:

$$1 - \frac{\text{Sample} - \text{Blank}}{\text{Control} - \text{Blank}}$$

$IC_{50}$ values were determined by plotting the log of the concentration of the test compound verses the percentage inhibition and fitting a straight line to the resulting data by using the least squares method.

The following examples illustrate the preparation of compounds of formula (I) and as such are not to be considered as limiting the invention set forth in the claims appended hereto.

EXAMPLE 1

Preparation of
(4S)-4-Thiophenoxymethyl-N-toluenesulfonyl-2-azetidinone

Step A: Preparation of
(4S)-4-Thiophenoxymethyl-2-azetidinone

To (4S)-4-Iodomethyl-2-azetidinone (408 mg) and potassium thiophenoxide (250 mg) in a 25 ml round-bottomed flask degassed to exclude oxygen was added dry DMF (3 ml). The resulting mixture was degassed again and covered with nitrogen. The mixture was heated at 90° under nitrogen for 56 hours. The mixture was then cooled to room temperature and diluted with water (20 ml). The resulting emulsion was extracted with methylene chloride (2×30 ml) and the organic layer washed with brine and dried ($Na_2SO_4$). Removal of solvent gave the crude product which was purified via preparative TLC using a silica gel plate (1500μ) [Rf=0.49; solvent system: 10% acetone in methylene chloride] to give the titled compound. 200 MHz NMR ($CDCl_3$): δ2.66(1H, dm), 2.8-3.4(3H, m), 3.89(1H, m), 6.1(1H, brs), 7.2-7.5(5H, m).

Step B: Preparation of
(4S)-4-Thiophenoxymethyl-N-toluenesulfonyl-2-azetidinone

To 4(S)-4-thiophenoxymethyl-2-azetidinone (40 mg) in 0.5 ml of 5% acetonitrile in methylene chloride containing 1% of tetrabutylammonium bromide (TBAB) was added excess toluenesulfonyl chloride and pulverized potassium hydroxide (ca. 30 mg). The mixture was stirred at room temperature for 2 hour and purified via preparative TLC using a silica gel plate (1500μ) [$R_f$=0.5; $CH_2Cl_2$] to give the titled compound. IR($CH_2Cl_2$): 1793 $cm^{-1}$; MS(FAB): 348 ($M^+ +1$); NMR ($CDCl_3$): δ2.45(3H, s), 2.72(1H, dd), 3.02(2H, m), 3.78(1H, dd), 4.12(1H, m) 7.2-7.5(7H, m), 7.84(2H, d).

EXAMPLE 2

Preparation of
(4S)-4-Phenylsulfoxymethyl-N-toluenesulfonyl-2-azetidinone

To (4S)-4-Thiophenoxymethyl-N-toluenesulfonyl-2-azetidinone (11 mg) in $CH_2Cl_2$ (1 ml) was added m-chloroperbenzoic acid (12 mg) (mCPBA) and the mixture stirred at room temperature overnight. The mixture was purified via preparative TLC on a silica gel plate and developed with 10% EtOAc in $CH_2Cl_2$. The sample was repurified by preparative TLC on a silica gel plate to give the titled product as a 1:1 mixture of α- and β-sulfoxides. NMR($CDCl_3$): δ2.44 and 2.45(3H, s), 4.08 and 4.47(1H, m), 7.74 and 7.91(2H, d).

EXAMPLE 3

Preparation of
(4S)-4-Phenylsulfonymethyl-N-toluenesulfonyl-2-azetidinone

To (4S)-4-Thiophenoxymethyl-N-toluenesulfonyl-2-azetidinone (6 mg) in $CDCl_3$ (1.6 ml) was added excess mCPBA. NMR showed the formation of the sulfone. The reaction mixture was added to hexane to the saturation point; the solid was filtered off and the filtrate purified by preparative TLC with 1-2% EtOAc in $CH_2Cl_2$ to yield the titled product: NMR ($CDCl_3$): δ2.47(3H, s), 3.20(2H, dd), 3.38(1H, dd), 4.14(1H, dd), 4.29(1H, m), 7.39(2H, d), 7.6-7.9(5H, m), 7.96(2H, d).

EXAMPLE 4

Preparation of
(4S)-4-p-Methoxycarbonylphenoxymethyl-N-toluenesulfonyl-2-azetidinone Step A: Preparation of
4(S)-4-p-Methoxycarbonylphenyoxymethyl-2-azetidinone To (4S)-4-Iodomethyl-2-azetidinone (204 mg) in dimethylformamide (DMF) (2 ml) was added methyl p-hydroxybenzoate (150 mg) and 97% NaH (24 mg). The mixture was heated at 80°-90° for 3 hours, and then evaporated to dryness and purified by preparative TLC on silica gel plates (1500μ) and developed with 10% acetone in $CH_2Cl_2$.

Step B: Preparation of
(4S)-4-p-Methoxycarbonylphenoxymethyl-N-toluensulfonyl-2-azetidinone To the product of Step (A) (9 mg) in TBAB stock solution (0.2 ml) (0.2 ml of 5% acetonitrile in methylene chloride containing 1% of tetrabutylammonium bromide) was added excess toluenesulfonyl chloride (TsCl) (~50 mg) and freshly pulverized KOH (~10 mg). The mixture was stirred overnight and then purified by preparative TLC on silica gel plates (1500μ) and developed with $CH_2Cl_2$ halfway and then 10% EtOAc/$CH_2Cl_2$ to yield the titled product. IR($CH_2Cl_2$): 1800 and 1718 $cm^{-1}$; MS(FAB): 390 ($M^+ +1$).

EXAMPLE 5

Preparation of
(±)-cis-3-Ethyl-4-methoxymethyl-N-toluenesulfonyl-2-azetidinone

To (±)-cis-3-Ethyl-4-hydroxymethyl-N-toluensulfonyl-2-azetidinone (18 mg) in $CH_2Cl_2$ at 0° to 5° C. was added boron trifluoride etherate solution (1 drop) and then diazomethane-ether solution dropwise (4 ml). The reaction mixture was purified by preparative TLC on a silica gel plate (1500μ) and developed with $CH_2Cl_2$ to afford the titled compound. NMR($CDCl_3$): δ1.04(3H, t), 1.54-1.92(2H, m) 2.45(3H, s), 3.16(1H, m), 3.26(3H, s), 3.70(2H, m ), 4.18(1H, m), 7.34(2H, d), 7.88(2H, d).

EXAMPLE 6

Preparation of (±)-4-(2-p-Methoxycarbonylphenoxy)ethyl-N-toluenesulfonyl-2-azetidinone

Step A: Preparation of Methyl p-(3-Butenyloxy)benzoate

A slurry of 4-bromo-1-butene (1.4 g), methyl p-hydroxybenzoate (1.5 g) and $K_2CO_3$ (1.8 g) in acetone was heated to reflux for 18 hours. The reaction was cooled, filtered, and concentrated to a yellow oil. The oil was chromatographed with 20% ethyl acetate/hexanes to give the titled compound.

NMR ($CDCl_3$): δ2.50–2.64(2H, m), 2.90(3H, s), 4.80(2H, t), 5.08–5.26(2H, m), 5.80–6.04(1H, m), 6.92(2H, d), 7.99(2H, d).

Step B: Preparation of (±)-4-(2-p-Methoxycarbonylphenoxy)ethyl-2-azetidinone The product from Step A (0.5 g) and chlorosulfonyl isocyanate (0.68 g) were stirred at 25° C. for 90 hours. The reaction was quenched with ethyl ether/water $Na_2SO_3$ (1.0 g), $K_2HPO_4$ (2.0 g) and stirred for 1 hour. The layers were separated and the aqueous layer was extracted with ethyl ether, dried ($Na_2SO_4$) and concentrated. Purification by column chromatographed with 20% ethyl acetate/hexanes afforded the titled compound.

NMR ($CDCl_3$): δ2.06–2.20(2H, m), 2.68–2.80(1H, m), 3.12–3.24(1H, m), 3.90(3H, s), 4.14(2H, t), 6.04–6.14(1H, bs), 6.90(2H, d), 8.0(2H, d).

Step C: Preparation of (±)-4-(2-p-Methoxycarbonylphenoxyethyl-N-toluenesulfonyl-2-azetidinone The product of Step B (10 mg) was dissolved in 19:1 $CH_2Cl_2:CH_3CN$ (1.6 ml) containing TBAB (1.6 mg). p-Toluenesulfonyl chloride (76 mg) was added followed by powdered KOH (16 mg). The mixture stirred under nitrogen for 1½ hours at 25°. The mixture was filtered through silica and concentrated. Purification by chromatography on silica gel, (25% ethyl acetate/hexane) afforded the titled compounds.

NMR ($CDCl_3$): δ2.10–2.30(1H, m), 2.46(3H, s), 2.56–2.72(1H, m) 2.96(1H, dd), 3.16(1H, dd), 3.90(3H, s), 4.16(2H, t), 6.80(2H, d) 7.25(H, d), 7.88(2H, d) 7.98(2H, d).

EXAMPLE 7

Preparation of (±)-4-(2-Benzyloxy)ethyl-N-toluenesulfonyl-2-azetidinone

Step A: Preparation of Benzyl 3-Butenyl Ether

NaH (0.24 g) was slowly added to a solution of 3-buten-1-ol (0.72 g) in DMF (15 ml) at 0° C., and the reaction stirred for 30 minutes. Benzyl bromide (1.9 g) was added and the reaction was stirred at 25° C. for 18 hours. The mixture was filtered and concentrated. The residue was dissolved in hexane, washed with water (3×), dried over $MgSO_4$, and concentrated. Purification by chromatography over silica gel (5% ethyl ether in hexane) afforded the titled compound.

NMR ($CDCl_3$): δ2.32–2.48(2H, m), 3.54(2H, t), 4.54(2H, s), 5.00–5.18(2H, m), 5.76–5.96(1H, m), 7.32–7.40(5H, m).

Step B: Preparation of (±)-4-(2-Benzyloxy)ethyl-2-azetidinone

The product from Step A (0.5 g) in chlorosulfonyl isocyanate (0.87 g) was stirred at 25° C. for 6 hours. The reaction was quenched in ether/water, $Na_2SO_3$, $K_2HPO_4$ and stirred for about 1 hour. The layers were separated and the aqueous layer was extracted with ethyl ether. The combined ether layers were washed with satd. NaCl, dried ($MgSO_4$) and concentrated. Purification by chromatography over silica gel (20% ethyl acetate/hexane) afforded the titled compound.

NMR($CDCl_3$): δ1.90–2.02(2H, m), 2.62–2.76 and 3.08–3.24(2H, m) 3.66(2H, t), 3.76–3.88(1H, m), 4.55(2H, s), 5.90–6.08(1H, bs), 7.34–7.54(5H, m).

Step C: Preparation of (±)-4-(2-Benzyloxy)ethyl-N-toluenesulfonyl-2-azetidinone The product of Step B (7.0 mg) was dissolved in 19:1 $CH_2Cl_2:CH_3CN$ (1.4 ml) containing TBAB (1.4 mg). p-Toluenesulfonyl chloride was added (15 mg) followed by KOH (913 mg) and the mixture stirred for 2 hours at 25° C. The mixture was filtered through silica gel, washed with $CH_2Cl_2$, ethyl acetate and concentrated. Purification by chromatography over silica gel (20% ethyl acetate/hexane) afforded the titled compound.

NMR ($CDCl_3$): δ1.82–2.04(2H, m), 3.24(3H, s), 2.86–3.14(2H, m), 3.60(2H, t), 4.10–4.24(1H, m), 4.46(2H, s), 7.22–7.42(7H, m), 7.88(2H, d).

EXAMPLE 8

Preparation of (±)-4-(2-Diphenylmethoxy)ethyl-N-toluenesulfonyl-2-azetidinone

Step A: Preparation of (±)-4-(2-Diphenylmethoxy)ethyl-2-azetidinone

To (±)-4-(2-hydroxy)ethyl-2-azetidinone (15 mg) in ether (3 ml) was added diphenyldiazomethane (35 mg). To this stirred solution was added dropwise $BF_3 \cdot (Et_2O)_2$ solution (3 drops). The violet color disappeared completely. Purification of the reaction mixture via preparative TLC gave the titled product.

Step B: Preparation of (±)-4-(2-Diphenylmethoxy)-ethyl-N-toluenesulfonyl-2-azetidinone A mixture of a TBAB stock solution (0.3 ml) in the presence of pulverized KOH (10 mg) and tosyl chloride (40 mg) was stirred at room temperature for 10–15 minutes. To this mixture was added the product of Step (A) (7.5 mg) and the mixture stirred at room temperature overnight. The reaction mixture was purified by preparative TLC on a silica gel plate (1000μ) and developed with 3% EtOAc in $CH_2Cl_2$ yielded the titled compound. NMR ($CDCl_3$): δ1.95(2H, m), 2.44(3H, s), 3.02(2H, ddd), 3.56(2H, t), 4.18(1H, m), 7.3(11H, m), 7.86(2H, d).

EXAMPLE 9

Preparation of (±)-cis-3-Ethyl-4-fluoromethyl-N-toluenesulfonyl-2-azetidinone

To (±)-cis-3-Ethyl-4-hydroxymethyl-N-toluenesulfonyl-2-azetidinone (3.9 mg) in $CH_2Cl_2$ (0.5 ml) was added diethylaminosulfur trifluoride (DAST) (15μl).

The mixture was stirred overnight under nitrogen. The mixture was purified by preparative TLC on a silica gel plate (1000μ) and developed with $CH_2Cl_2$ to give the titled compound. NMR($CDCl_3$): δ1.06(3H, t), 1.6–2.0(2H, m), 2.45(3H, s), 3.26(1H, dt), 4.27(1H, dm), 4.65(1H, m), 4.88(1H, m), 7.37(2H, d), 7.88(2H, d)

EXAMPLE 10

Preparation of
(±)-cis-3-Ethyl-4-(2-p-methoxycarbonylphenoxy)ethyl-N-toluenesulfonyl-2-azetidinone

Step A: Preparation of (±)-cis-3-Ethyl-4-(2-t-butyldiphenylsilyloxy)ethyl-2-azetidinone To 7.09 ml of 1,1,1,3,3,3-hexa-methyldisilazane in 25 ml of anhydrous THF was added 25.2 ml of 1.6M n-butyllithium in hexane at −70° C. The resulting solution was stirred for 30 minutes at −70° C. and 10 g of 3-t-butyldiphenylsilyloxypropanal in 10 ml of THF was added dropwise. The mixture was stirred for 1.5 hours at −70° C. and the resulting cold solution of N-trimethylsilylimine was used directly in the following reaction.

To a solution of LDA (generated from 4.48 ml of diisopropylamine and 24 ml of 1.6M n-butyllithium) in 50 ml of THF at −70° C. was added 4.24 ml of ethyl butyrate in 8 ml of THF. The resulting solution was stirred for 1 hour at −70° C. followed by the addition of the above silylimine solution. The mixture was stirred for 1 hour at −70° C. then 2 hours at room temperature. The solution was worked up by the addition of 200 ml of ether then extracted with 3×50 ml of 1.5M HCl and 2×50 ml of $H_2O$. The aq. solution was extracted with 3×50 ml of ether. The organic layers were combined, dried and concentrated. The product was purified by flash column chromatography (30% EtOAc in hexane) to give the cis compound and the trans compound. $^1$H NMR($CDCl_3$): δ0.86–1.16(12H, m), 1.36–1.86(4H, m), 3.09(1H, m), 3.60–3.84(3H, m), 5.73(1H, broad) 7.28–7.48(6H, m), 7.50–7.74(4H, m) for the cis compound.

Step B: Preparation of (±)-cis-3-Ethyl-4-(2-hydroxy)ethyl-2-azetidinone

To 650 mg of the Step A product in 10 ml of methanol was added 4 ml of HF. The mixture was stirred for 2 hours at room temperature. Satd. $NaHCO_3$ was added until bubbling ceased and the aq. solution was extracted with hexane (3×60 ml). The solution was filtered and the filtrate was concentrated under vacuum. The residue was dissolved in $CH_2Cl_2$, filtered and the filtrate was concentrated in vacuo to yield the titled compound. $^1$H NMR ($CDCl_3$): δ1.05(3H, t), 1.47–1.97(4H, m), 2.25(1H, broad), 3.05–3.23(1H, m), 3.61–3.99(3H, m), 6.41(1H, broad).

Step C: Preparation of (±)-cis-3-Ethyl-4-(2-toluenesulfonyloxy)ethyl-2-azetidinone To 60 mg of the Step B product in 4 ml of $CH_2Cl_2$ was added 0.120 g of tosyl chloride and 0.08 ml of pyridine. The mixture was stirred for 2 hours at room temperature. The product was purified by preparative TLC (50% EtOAc in hexane). $^1$H NMR($CDCl_3$): δ1.04(3H, t), 1.44–1.98(4H, m), 2.46(3H, s), 3.06–3.18 (1H, m), 3.74–3.81(1H, m), 4.14(2H, t), 5.96(1H, broad), 7.36(2H, d), 7.78(2H, d).

Step D: Preparation of (±)-cis-3-Ethyl-4-(2-p-methoxycarbonylphenoxy)ethyl-2-azetidinone To 7 mg of the Step C product in 2 ml of acetone was added 20 mg of methyl p-hydroxybenzoate and 20 mg of potassium carbonate. The mixture was refluxed for 2 hours and the resulting product purified by preparative TLC (25% EtOAc in $CH_2Cl_2$). $^1$H NMR($CDCl_3$): δ1.11(3H, t), 1.63–1.92(2H, m), 1.94–2.18(2H, m), 3.12–3.24(1H, m), 3.83–3.97(4H, s+m) 4.05–4.20(2H, m), 6.02(1H, broad), 6.89(2H, d), 7.99(2H, d).

Step E: Preparation of (±)-cis-3-Ethyl-4-(2-p-methoxycarbonylphenoxy)ethyl-N-toluenesulfonyl-2-azetidinone To 4 mg of the Step D product in 1 ml of TBAB stock solution was added a small amount of tosyl chloride and potassium hydroxide. The resulting mixture was stirred for 30 minutes at room temperature and the product was isolated by preparative TLC (30% EtOAc in hexane).

$^1$H NMR($CDCl_3$): δ1.09(3H, t), 1.62–1.86(2H, m), 2.12–2.50(5H, s+m), 3.02–3.24(1H, m), 3.88(3H, m), 4.04–4.39(3H, m), 6.91(2H, d), 7.31(2H, d), 7.81(2H, d), 8.01(2H, d).

EXAMPLE 11

Preparation of
(±)-3-Ethyl-4-(2-phenylsulfonyl)ethyl-N-toluenesulfonyl-2-azetidinone

Step A: (±)-cis-3-Ethyl-4-(2-thiophenoxy)ethyl-2-azetidinone

To 8 mg of the titled product of Example 10 Step C in 1 ml of absolute ethanol was added a small amount of potassium thiophenol. The resulting mixture was refluxed for ½ hour and the product purified by preparative TLC (30% EtOAc in hexane). $^1$H NMR ($CDCl_3$): δ1.04(3H, t), 1.46–1.98(4H, m), 2.97(2H, t), 3.06–3.16(1H, m), 3.77–3.85(1H, m), 5.99 (1H, broad), 7.16–7.36(5H, m).

Step B: (±)-cis-3-Ethyl-4-(2-thiophenoxy)ethyl-N-toluenesulfonyl-2-azetidinone To 3.5 mg of the Step A product in 1 ml of TBAB stock solution was added a small amount of powdered KOH. After 2 minutes of stirring a small amount of tosyl chloride was added. The mixture was stirred for ½ hour at room temperature. The product was purified by preparative TLC (30% EtOAc in hexane). $^1$H NMR ($CDCl_3$): δ1.01(3H, t), 1.44–1.78 (3H, m), 1.82–2.04(1H, m), 2.14–2.34(1H, m), 2.45(3H, s), 3.02–3.16(2H, m), 4.23(1H, q), 7.18–7.42(7H, m), 7.80–7.89(2H, d).

Step C: Preparation of (±)-3-Ethyl-4-(2-phenylsulfonyl)ethyl-N-toluenesulfonyl-2-azetidinone To 3 mg of the Step B product in 1 ml of $CH_2Cl_2$ was added a small amount of mCPBA. The mixture was stirred for ½ hour at room temperature. The product was purified by preparative TLC (30% EtOAc in hexane). $^1$H NMR($CDCl_3$): δ1.04(3H, t), 1.44–1.82(3H, m), 2.16–2.32(1H, m), 2.45(3H, s), 3.04–3.20(1H, m), 3.36–3.52(2H, dd), 4.18–4.32(1H, q), 7.28–7.30(2H, d) 7.56–7.98(7H, m).

EXAMPLE 12

Preparation of
(3R,4R,5'R)-(E,E)-3-Methoxymethyl-4-(10'-methoxycarbonyl-5',7',9'-trimethyl-7',9'-decadienyl)-N-toluenesulfonyl-2-azetididione)

Step A: Preparation of (2'R,3'R,7R)-(E,E)-Methyl 11-[3'-(hydroxymethyl]-4'-oxo-2'-oxetanyl-3,5,7-trimethyl-2,4-undecadienoate To a solution of (E,E)-11-[3'-(hydroxymethyl]-4'-oxo-2'-oxetanyl-3,5,7-trimethyl-2,4-undecadienoic acid (2.6 g) in ether (~30 ml) was added diazomethane. The mixture was stirred for 18 hours at 25° C. The reaction mixture was purged with nitrogen for about 1 hour then washed with saturated NaCl, dried (MgSO₄) and concentrated to a light yellow oil. The crude product was used in the next step without further purification.

Step B: Preparation of (2'R, 3'R, 7R)-(E,E)-Methyl 11-[3'-(Methoxymethyl)-4'-oxo-2'-oxetanyl]3,5,7-trimethyl-2,4-undecadienoate The product of Step A was taken up in 25 ml ether then methyl iodide (10.7 g) and silver oxide (4.4 g) were added. The reaction was heated to 47° C. for 5 hours, and then stirred for 18 hrs at 25° C. The reaction mixture was filtered and concentrated. Purification by chromatography over silica gel (1.5% methanol/methylene chloride) afforded the titled compound.
NMR(CDCl₃): δ0.84(3H, d), 1.80(3H, d), 2.22(3H, d), 3.40(3H, s), 3.70(3H, s), 4.45–4.56(1H, m), 5.67(1H, s), 5.70(1H, s).

Step C: Preparation of (2R, 3R, 8R)-N-2',4'-Dimethoxybenzyl 2-Methoxymethyl-3-hydroxy-8,10,12-trimethyl-14-methoxycarbonyl-10,12-tridecadienamide The product of Step B (3.02 g), 2,4-dimethoxybenzylamine (4.3 g) in DMF (10 ml) and water (4 ml) were heated to 100° C. for 3 hours. The reaction mixture was quenched with H₂O (~40 ml) and extracted with ethyl acetate (3×100 ml), dried (MgSO₄) and concentrated to a yellow oil. The oil was dissolved in ethyl acetate and washed with H₂O (4×), saturated NaCl (1×) then concentrated under vacuum. The titled compound was used without further purification.
NMR (CDCl₃): δ0.80(3H, d), 1.78(3H, s), 2.24(3H, s), 3.32(3H, s), 3.70(3H, s), 3.80(3H, s), 3.82(3H, s), 5.66(1H, s), 5.69(1H, s), 6.36–6.48(2H, m), 6.60–6.70 (1H, m), 7.12(1H, d).

Step D: Preparation of (2R,3R,8R)-N-2',4'-Dimethoxybenzyl 2-Methoxymethyl-3-methanesulfonyl-5,10,12-trimethyl-14-methoxycarbonyl-10,12-tridecadienamide.

To the product of Step C (4.4 g) in pyridine (20 ml) at 0° was added methanesulfonyl chloride (2.4 g) dropwise over 10 minutes. The reaction mixture was stirred for 2 hours at 0° C. and then quenched with H₂O, extracted with CH₂Cl₂ (3×), washed with saturated NaCl, dried (MgSO₄) and concentrated. Purification by chromatography over silica gel (3% ethyl ether/methylene chloride) afforded the titled compound.
NMR (CDCl₃): δ0.80(3H, d), 1.79(3H, s), 2.24(3H, s), 2.86(3H, s), 3.26(3H, s), 3.70(3H, s), 3.80(3H, s), 3.84(3H, s), 5.66(1H, s), 5.69(1H, s), 6.36–6.50(2H, m), 6.58–6.70(1H, m), 7.14(1H, d).

Step E: Preparation of (2R,3S,8R)-N-2',4'-Dimethoxybenzyl 2-Methoxymethyl-3-bromo-8,10,12-trimethyl-14-methoxycarbonyl-10,12-tridecadienamide To a solution of the product from Step D (2.6 g) in DMF (10 ml) was added NaBr (0.48 g). The reaction mixture was stirred under nitrogen for 1¼ hours at 100° C. The reaction mixture was quenched into H₂O/ethyl acetate and the aqueous layer extracted with ethyl acetate (2×), then washed with H₂O (3×), saturated NaCl, dried (MgSO₄) and concentrated to a light yellow oil. Purification by chromatography over silica gel (gradient of 20 to 50% ethyl acetate/hexane) afforded the titled compound.
NMR (CDCl₃): δ0.80(3H, d), 1.80(3H, s), 2.24(3H, s), 2.58–2.70(1H, m), 3.36(3H, s), 3.70(3H, s), 3.80(3H, s), 3.84(3H, s), 5.66(1, s), 5.69(1H, s), 6.36–6.48(2H, m), 6.64–6.78(1H, m), 7.16(1H, d).

Step F: Preparation of (3R,4R,5'R)-(E,E)-3-Methoxymethyl-4-(10'-methoxycarbonyl-5',7',9'-trimethyl-7',9'-decadienyl)-N-2,4-dimethyoxybenzyl-2-azetidinone To the product of Step E (595 mg) in 42 ml of 19:1 CH₂Cl₂:CH₃CN containing 1 mg/ml of TBAB was added freshly powdered KOH (~200 mg); the reaction was stirred for 18 hours at 25° C., filtered and concentrated. Purification by chromatography over silica gel (gradient of 20 to 50% ethyl acetate/hexane) afforded the titled compound.
NMR (CDCl₃): δ0.80(3H, s), 1.80(3H, d), 2.24(3H, d), 2.90–3.00(1H, m), 3.36(3H, s), 3.70(3H, s), 3.80(6H, s), 5.68(1H, s), 5.71(1H, s), 6.40–6.50(2H, m), 7.16(1H, d).

Step G: Preparation of (3R,4R,5'R)-(E,E)-3-Methoxymethyl-4-(10'-methoxycarbonyl-5',7',9'-trimethyl-7',9'-decadienyl)-2-azetidinone To a solution of the Step F product (166 mg) in THF (44 ml) at 0° C. was added (NH₄)₂Ce(NO₃)₆ (440 mg) in H₂O (4.4 ml) over 1.25 hrs. The reaction mixture was stirred for 18 hours at 25° C., extracted with ethyl acetate (3×) saturated NaCl(1×) dried (MgSO₄) and concentrated to an oil. Purification by chromatography over silica gel (40% ethyl acetate/hexane) afforded the titled compound.
NMR (CDCl₃): δ0.82(3H, s), 1.78(3H, d), 2.22(3H, d), 2.94–3.00(1H, m), 3.28(3H, s), 7.70(3H, s), 5.65(1H, s), 5.68(1H, s), 5.78–5.84(1H, b s).

Step H: Preparation of (3R,4R,5'R)-(E,E)-3-Methoxymethyl-4-(10'-methoxycarbonyl-5',7',9'-trimethyl-7',9'-decadienyl)-N-toluensulfonyl-2-azetidinone To a solution of the Step G product in 350 μl of 19:1 CH₂Cl₂: CH₃CN containing 1 mg/ml of TBAB (0.35 mg) was added p-toluenesulfonyl chloride (16.7 mg) followed by powdered KOH (5 mg). The reaction mixture was stirred for 1.5 hours, filtered, washed with ethyl acetate, and concentrated. Purification by chromatography over silica gel (25% ethyl acetate/hexane) afforded the titled compound.
NMR (CDCl₃): δ0.82(3H, s), 1.78(3H, d), 2.23(3H, d), 2.24(3H, s), 2.96–3.02(1H, m), 3.18(3H, s), 3.70(3H, s), 5.66(1H, s), 5.69(1H, s), 7.32(2H, d), 7.85(2H, d)

What is claimed is:
1. A compound of structural formula (I):

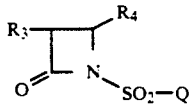
(I)

wherein:
Q is
- a) $C_{1-5}$ alkyl; $C_{6-10}$ aryl;
- c) $C_{7-15}$ aralkyl;
- d) $C_{6-10}$ aryl substituted with W;
- e) $C_{7-15}$ aralkyl wherein the aryl moiety is substituted with W; or
- f) OH;

$R_3$ is
- a) H;
- b) $C_{1-5}$ alkyl; or
- c) $C_{1-5}$ alkoxyCH$_2$—;

$R_4$ is —(CH$_2$)$_n$ R;
R is a) 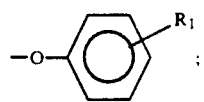

b) 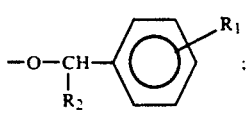

c) 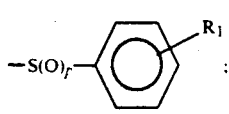

- d) —O—$C_{1-5}$ alkyl;
- e) halogen; or

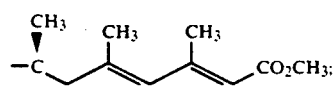

$R_1$ is
- a) H;
- b) $C_{1-5}$ alkyl; or
- c) —CO$_2$C$_{1-5}$ alkyl;

$R_2$ is
- a) H; or

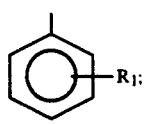

n is 1 to 4,
provided that when R is

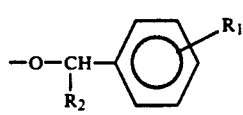

n is 2;
p is 0 to 2;

halogen is F, Cl, Br or I;
W is
- a) $C_{1-5}$ alkyl;
- b) $C_{1-5}$ alkoxy;
- c) —CO$_2$C$_{1-5}$ alkyl; or
- d) —NO$_2$.

2. A compound of claim 1 wherein: n is 1.

3. A compound of claim 2 wherein $R_3$ is H, and R is a) 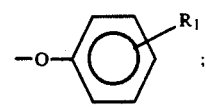

b) 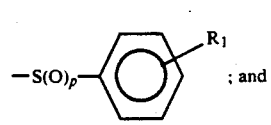; and c) halogen;

Q is

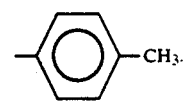

4. A compound of claim 3 wherein the configuration at the 4-position of the lactam ring is S; and
R is:

i) 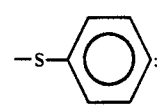

ii) 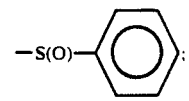

iii) 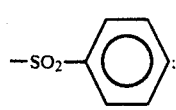

iv) 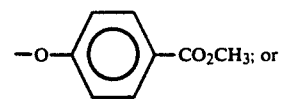

v) iodide

5. A compound of claim 2 wherein $R_3$ is $C_{1-5}$ alkyl.

6. A compound of claim 5 wherein R is a) 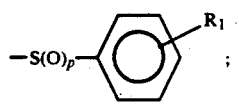

- b) $C_{1-5}$ alkoxy;
- c) halogen;

Q is

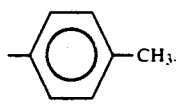

7. A compound of claim 6 wherein the configuration at the 3,4 positions is cis; and
   i) $R_3$ is $CH_3CH_2$, R is

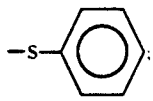

ii) $R_3$ is $CH_3CH_2$, R is $-O-CH_3$;
   iii) $R_3$ is $CH_3CH_2$, R is F.
8. A compound of claim 1 wherein n is 2.
9. A compound of claim 8 wherein $R_3$ is H and R is:

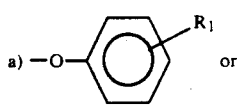

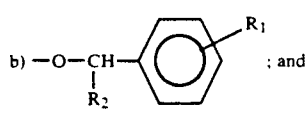

10. A compound of claim 9 wherein; R is:

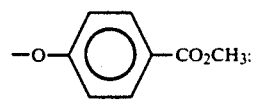

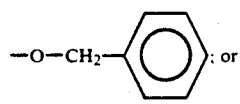

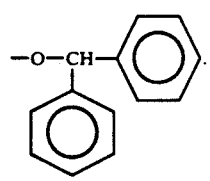

11. A compound of claim 8 wherein $R_3$ is $CH_3CH_2-$ or $CH_3O-CH_2-$; and R is:

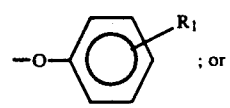

-continued

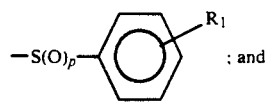

Q is

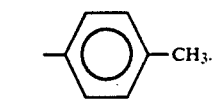

12. A compound of claim 11 wherein:
   i) $R_3$ is $CH_3CH_2-$, R is

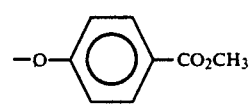

and the configuration at the 3,4 position is cis;
   ii) $R_3$ is $CH_3OCH_2-$, R is

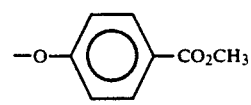

and the configuration at the 3,4 position is trans;
   iii) $R_3$ is $CH_3CH_2-$, R is

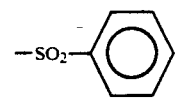

and the configuration at the 3,4 position is cis.
13. A compound of claim 1 wherein n is 3; and R is

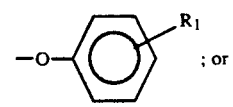

b) halogen; and
Q is

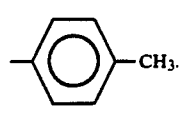

14. A compound of claim 13 wherein $R_3$ is H; and R is:

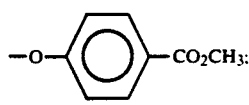

-continued

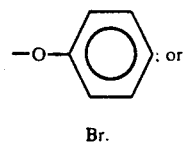

Q is ii)

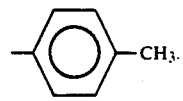

iii)

17. A compound of claim 16 which is

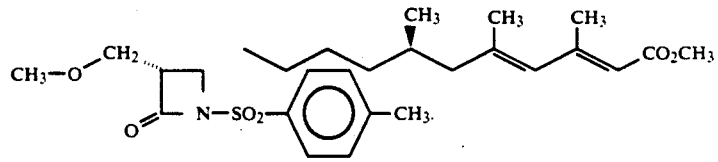

15. A compound of claim 1 wherein n is 4.
16. A compound of claim 15 wherein: $R_3$ is H or $C_{1-5}$ alkoxyCH$_2$— and
R is

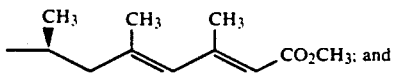

18. A hypocholesterolemic pharmaceutical composition which comprises a therapeutically effective amount of a compound of claim 1 and a pharmaceutically acceptable carrier.

19. A method of treating hypercholesterolemia which comprises the administration to a subject in need of such treatment of a therapeutically effective amount of a compound of claim 1.

* * * * *